United States Patent [19]

Foley et al.

[11] 3,931,260

[45] Jan. 6, 1976

[54] ORGANO METALLIC COMPOUNDS

[75] Inventors: Kevin M. Foley, Hebron; Francesco M. Vigo, Heath, both of Ohio

[73] Assignee: Owens-Corning Fiberglas Corporation, Toledo, Ohio

[22] Filed: Feb. 22, 1974

[21] Appl. No.: 445,015

[52] U.S. Cl.... 260/429.3; 117/126 GQ; 260/429 R; 260/429.5; 260/429.7; 260/446
[51] Int. Cl.² ............................................ C07F 7/00
[58] Field of Search.............. 260/429.3, 429.5, 446, 260/429.7, 429

[56] References Cited
UNITED STATES PATENTS

| | | | |
|---|---|---|---|
| 2,511,013 | 6/1950 | Rust et al............................ | 260/446 |
| 2,512,063 | 6/1950 | Kveidl et al................... | 260/429.3 X |
| 2,709,174 | 5/1955 | Rust et al.......................... | 260/429.5 |
| 2,883,348 | 4/1959 | Pechukas.......................... | 260/429.5 |
| 3,031,425 | 4/1962 | Schoepfle et al. .............. | 260/446 X |
| 3,081,327 | 3/1963 | Birum et al.......................... | 260/446 |
| 3,190,892 | 6/1965 | Richardson et al.............. | 260/429 X |
| 3,203,812 | 8/1965 | Emblem et al................ | 260/429.3 X |
| 3,471,411 | 10/1969 | Bowman et al.................. | 260/446 X |
| 3,781,315 | 12/1973 | Pepe et al......................... | 260/429.7 |

OTHER PUBLICATIONS

Glockling, The Chemistry of Germanium, Academic Press, London, p. 38 (1969).
Lesbre et al., The Organic Compounds of Germanium, John Wiley & Sons, N.Y., pp. 431–433 (1971).
Feld, The Organic Chemistry of Titanium, Butterworths, Washington, p. 22 (1965).

*Primary Examiner*—Helen M. S. Sneed
*Attorney, Agent, or Firm*—Carl G. Staelin; John W. Overman; Keith V. Rockey

[57] ABSTRACT

Organo metallic compounds for use in the treatment of glass fibers prepared by reaction of a hydrolyzable metal halide and one or more epoxides. The organo metallic compounds of this invention are characterized by a beta-haloalkoxy group and are resistant to hydrolysis.

16 Claims, No Drawings

ORGANO METALLIC COMPOUNDS

This invention relates to complex organo metallic compounds and more particularly to complex organo metallic compounds which are resistant to hydrolysis for use in the treatment of glass surfaces.

It has been common practice for a number of years to treat glass surfaces with organo metallic compounds to impart improved abrasion resistance to the glass surfaces. For example, it has been proposed to treat glass surfaces with ortho esters of titanium, $$Ti(OR)_4 \quad (1)$$

wherein R is an organic group, and then heat the glass surfaces to an elevated temperature to convert the ortho ester to $TiO_2$. The $TiO_2$ coating may, if desired, be overcoated with a protective binder to assume adhesion to the glass fiber surface as described in U.S. Pat. No. 3,352,708.

One of the primary difficulties with such titanium compounds is that they are quite readily hydrolyzable and even hydrolyze in response to moisture in air. In an effort to avoid such difficulties, it has been suggested in U.S. Pat. No. 3,582,395 to treat glass fibers with a titanium compound which is more resistant to hydrolysis, such as titanium ortho esters in which the compound contains an organo silane group $$Ti(O-SiR_3)_4$$

wherein R is an organic group such as an alkyl group or the like. Such compounds are quite expensive to prepare and employ because of the organo silane compounds which must be used in their preparation.

It is accordingly an object of the present invention to provide organo metallic compounds which are resistant to hydrolysis and can be prepared in a simple and inexpensive manner.

It is a further object of the present invention to provide organo metallic compounds which are resistant to hydrolysis and can be used in the treatment of glass surfaces, including glass fibers, to impart improved abrasion resistance to the glass and to impart hydrophobicity to the glass surface.

The concepts of the present invention reside in organo metallic compounds in the form of ortho esters which contain a halogen atom in the beta-position relative to the oxygen - metal bond. These compounds are characterized by a beta-haloalkoxy group $$M-O-\underset{X}{\underset{|}{C}}-\underset{|}{C}- \quad (3)$$

wherein M is a metal and X is a halogen atom. It has been found that the presence of the beta-haloalkoxy group imparts improved resistance to hydrolysis. Without limiting the present invention as to theory, it is believed that the halogen atom stabilizes the bond between the metal and the oxygen atom.

The concepts of the present invention are applicable to a number of polyvalent metals, and particularly those which form highly hydrolyzable halide salts. Preferred in this invention is titanium, but use can also be made of tin, germanium, zirconium and antimony.

In the practice of the invention, the organo metallic compounds are prepared by reaction of one of the foregoing metals in the form of the hydrolyzable halide, and preferably chloride or bromide, with an epoxide $$MX_n + CH_2-\underset{\underset{O}{\diagdown\diagup}}{C}- \longrightarrow M(O-CH_2-\underset{\underset{X}{|}}{\overset{|}{C}}-)_n \quad (4)$$

wherein n is the valence of the metal, 3 or 4.

As the epoxide which is reacted with the metal halide, use can be made of a number of epoxides including alkylene oxides $$CH_2-\underset{\underset{O}{\diagdown\diagup}}{CH}-R \quad (5)$$

wherein R is hydrogen or alkyl containing 1 to 10 carbon atoms (e.g., ethylene oxide, propylene oxide, butylene oxide, etc.). It is also possible, and sometimes desirable, to employ epoxides containing one or more functional groups. By way of illustration, the following compounds can be employed:

[1] Epoxides of the formula $$CH_2-\underset{\underset{O}{\diagdown\diagup}}{CH}-CH_2-O-R_2 \quad (6)$$

wherein $R_2$ is an aryl group such as phenyl or phenyl substituted with an amino group, a halogen group, an alkyl group; alkyl containing 1 to 20 carbon atoms and substituted derivatives thereof; an alkenyl group containing 2 to 8 carbon atoms (e.g., vinyl, allyl, etc.); a group having the formula $$CH_2=\underset{\underset{R'}{|}}{C}-\overset{\overset{O}{\|}}{C}- \quad (7)$$

wherein R' is hydrogen or methyl. Illustrative of such epoxides are phenyl glycidyl ether, cresyl glycidyl ether, allyl glycidyl ether, glycidyl acrylate, glycidyl methacrylate, a mixture of n-octyl and n-decyl glycidyl ethers (Epoxide No. 7 from Procter and Gamble) and a mixture of n-dodecyl and n-tetradecyl glycidyl ethers (Epoxide No. 8 from Procter and Gamble).

[2] Epoxides of the formula $$CH_2-\underset{\underset{O}{\diagdown\diagup}}{CH}-CH_2-R_3-CH_2-\underset{\underset{O}{\diagdown\diagup}}{CH}-CH_2 \quad (8)$$

wherein $R_3$ is a divalent organic radical such as alkylene containing 1 to 10 carbon atoms; alkylene-oxyalkylene containing 2 to 20 carbon atoms, oxyalkyleneoxy containing 1 to 10 carbon atoms; oxyalkylene-oxyalkyleneoxy containing 2 to 20 carbon atoms; divalent aromatic groups such as a group of the formula $$-O-\underset{}{\phantom{X}}\!\!\!\bigcirc\!\!\!-\underset{\underset{CH_3}{|}}{\overset{\overset{CH_3}{|}}{C}}-\!\!\!\bigcirc\!\!\!-O-$$

or $$-O-\underset{}{\bigcirc}\overset{-O-}{}$$

A number of such epoxides are commercially available from Dow and Ciba and include the following:

$$CH_2\!\!-\!\!CH\!-\!CH_2\!-\!O\!-\!(CH_2)_4\!-\!O\!-\!CH_2\!-\!CH\!\!-\!\!CH_2 \quad (11)$$
$$\underset{O}{\diagdown\!\diagup} \qquad\qquad\qquad\qquad\qquad \underset{O}{\diagdown\!\diagup}$$

(RD 2)

$$CH_2\!\!-\!\!CH\!-\!CH_2\!-\!O\!-\!(CH_2\!-\!CH_2\!-\!O)_{1.36}\!-\!CH_2\!-\!CH\!\!-\!\!CH_2 \quad (12)$$

(DER 736)

$$CH_2\!\!-\!\!CH\!-\!CH_2\!-\!O\!-\!(CH_2\!-\!CH_2\!-\!O)_{4.31}\!-\!CH_2\!-\!CH\!\!-\!\!CH_2 \quad (13)$$

(DER 732)

$$CH_2\!\!-\!\!CH\!-\!CH_2\!-\!O\!-\!(CH_2\!-\!CH_2\!-\!O)_{6.58}\!-\!CH_2\!-\!CH\!\!-\!\!CH_2 \quad (14)$$

(DER 508)

(DER 332) (15)

(ERE 1359) (16)

[3] Cycloalkane epoxides, including the following:

(RD 4 or ERL 4206) (17)

(ERR 4205) (18)

(FRR 4289) (19)

(ERR 4221) (20)

In the preparation of the organo metallic compounds of this invention, the reactants are simply contacted in the liquid phase, either with or without an inert organic solvent. The temperature of the reaction is not critical to the practice of the invention, and the reaction frequently evolves heat. For best results, use can be made of a reaction temperature within the range of 0° to 100°C, although higher temperatures may be employed. When the solvent is employed, it is an aprotic solvent; good results have been obtained with liquid alkanes (e.g., pentane, hexane, heptane, etc.) and aromatic hydrocarbons (e.g., benzene, toluene, xylene, etc.).

The metal halides preferred for use in the invention are tetravalent titanium halides, e.g., $TiCl_4$ or $TiBr_4$. Use can also be made of $SnCl_4$, $SnBr_4$, $GeCl_4$, $GeBr_4$, $ZrCl_4$, $ZrBr_4$, $SbCl_3$ or $SbBr_3$.

The relative proportions of reactants depend not only on the valence of the metal halide but also on the nature of the epoxide. When the epoxide contains only one oxirane ring, the epoxide should be employed in an amount sufficient to displace all of the halogen atoms from the metal halide. Good results are frequently obtained when the mole ratio of epoxide to halogen in the metal halide is within the range of 0.8 to 1.8, and preferably 0.9 to 1.3.

Compounds which can be prepared using alkylene oxides have the general formula $$M(O\!-\!CH_2\!-\!\underset{X}{CH}\!-\!R)_n \qquad (21)$$

wherein M is titanium, tin, germanium or zirconium and n is 4, or M is antimony and n is 3.

Representative compounds include the following:

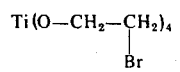 (22)

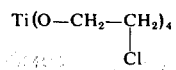 (23)

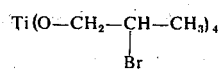 (24)

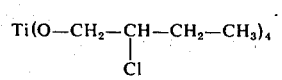 (25)

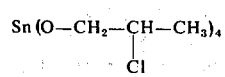 (26)

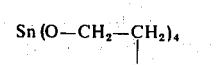 (27)

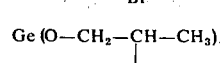 (28)

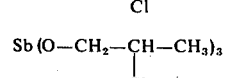 (29)

Compounds which can be prepared from the functional epoxides described above have the general formula

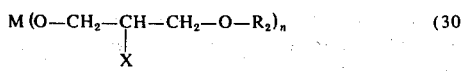 (30)

wherein M, X, n and $R_2$ are as defined above. Representative of such compounds include:

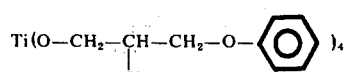 (31)

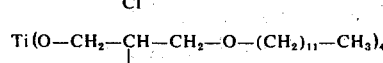 (32)

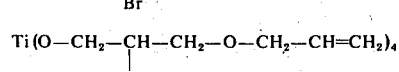 (33)

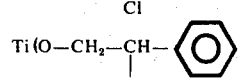 (34)

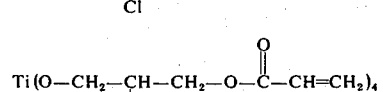 (35)

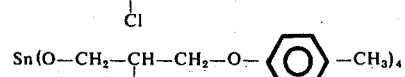 (36)

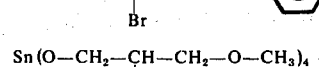 (37)

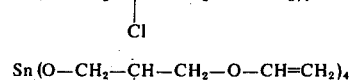 (38)

 (39)

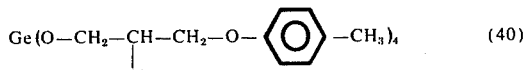 (40)

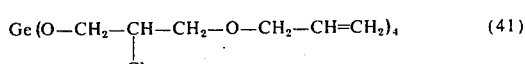 (41)

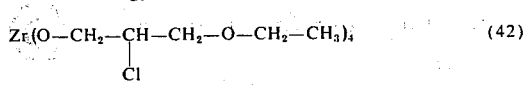 (42)

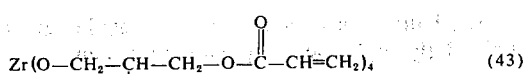 (43)

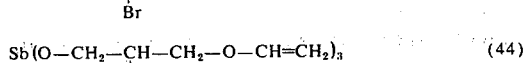 (44)

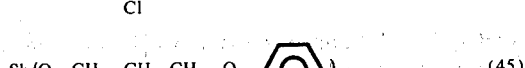 (45)

It is possible, and frequently desirable, to employ a combination of monoepoxides of the type described above. For example, use can be made of an alkylene oxide and an epoxide containing a functional group in accordance with the following reaction:

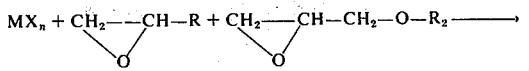
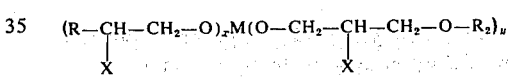 (46)

wherein x and y are integers, the sum of which is equal to the valence of the metal halide, n, depending on the reaction proportions. In practice, the reaction product is most frequently a mixture which can be utilized as such without the need to separate particular compounds.

However, specific compounds contained in the reaction product can be, if desired, separated therefrom by known techniques, such as fractional distillation, liquid chromatography, etc., to yield substantially pure compounds. The nature of the specific compounds, of course, depends on the porportions.

For example, when the reaction mixture contains 1 to 3 epoxide equivalents of the functional monoepoxide, the reaction product, for a tetravalent metal halide, includes the following compounds

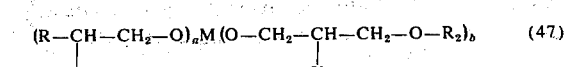 (47)

wherein a and b are integers from 1 to 3, with the total of a and b being equal to 4. When the metal is antimony, the compounds are the same except that a and b are each integers from 1 to 2 and their sum is equal to 3.

Examples of specific compounds which can be prepared in accordance with the concepts of the invention include the following, it being understood that the raw reaction product prior to separation is a mixture.

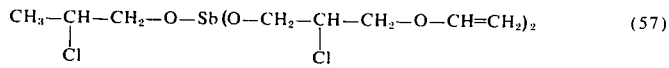

(57)

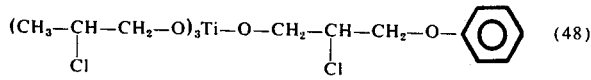

(48)

(TiCl₄ 1 mole; propylene oxide 3 epoxide equivalents; phenyl glycidyl ether 1 epoxide equivalent)

(CH₂Cl—CH₂O)₃Ti—O—CH₂—CH—CH₂—O—C—CH=CH₂ (49)

(TiCl₄ 1 mole; ethylene oxide 3 epoxide equivalents; glycidyl acrylate 1 epoxide equivalent)

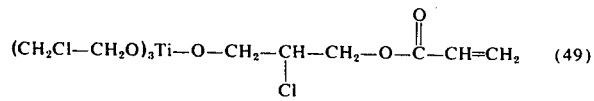

(50)

(TiCl₄ 1 mole; propylene oxide 2 epoxide equivalents; allyl glycidyl ether 2 epoxide equivalents)

(CH₂Cl—CH₂—O)₃Sn—O—CH₂—CH—CH₂—O—C₈H₁₇ (51)

(SnCl₄ 1 mole; ethylene oxide 3 epoxide equivalents; n-octyl glycidyl ether 1 epoxide equivalent)

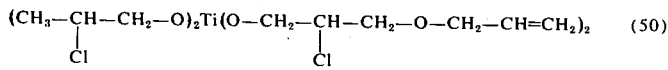

(52)

(SnBr₄ 1 mole; propylene oxide 2 epoxide equivalents; cresyl glycidyl ether 2 epoxide equivalents)

(CH₂Cl—CH₂—O)₃Ge—O—CH₂—CH—CH₂—O—CH=CH₂ (53)

(GeCl₄ 1 mole; ethylene oxide 3 epoxide equivalents; vinyl glycidyl ether 1 epoxide equivalent)

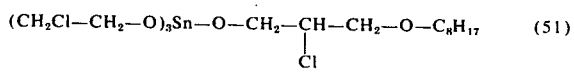

(54)

(GeCl₄ 1 mole; butylene oxide 1 epoxide equivalent; methyl glycidyl ether 3 epoxide equivalents)

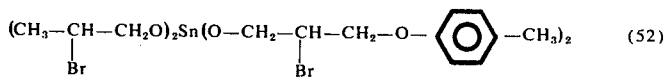

(55)

(ZrCl₄ 1 mole; propylene oxide 3 epoxide equivalents; glycidyl methacrylate 1 epoxide equivalent)

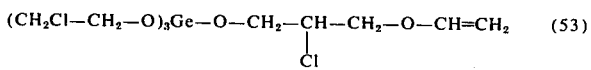

(56)

(SbCl₄ 1 mole; ethylene oxide 2 epoxide equivalents; phenyl glycidyl ether 1 epoxide equivalent)

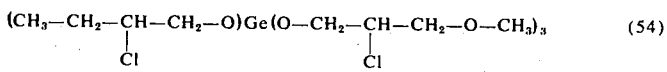

(SbCl₄ 1 mole; propylene oxide 1 epoxide equivalent; vinyl glycidyl ether 2 epoxide equivalents)

The products of the above reactions are, as indicated above, mixtures; the foregoing compounds can be, if desired, isolated from such mixtures.

Where use is made of an epoxide containing more than one oxirane ring, it is desirable to employ a combination of epoxides, one having more than one oxirane group and one having but a single oxirane group, to avoid gelling of the product. In actual practice, it has been found that best results are usually obtained where the monoepoxide is reacted with the metal halide, and the product is then reacted with the diepoxide. The product produced is generally a mixture of compounds which can be utilized as such without the need to separate compounds contained in the product. However, compounds contained in the reaction product can be, if desired, separated from the mixture by known techniques.

As with compounds described above, the nature of such compounds depends on the relative proportions. It has been found that use should be made of at least 2.2 and preferably 2.5 epoxide equivalents of the monoepoxide per mole of tetravalent metal halide, and at least 1.7 epoxide equivalents of the monoepoxide per mole of the trivalent metal halide. It is generally preferred to employ 2.2 to 3.5 epoxide equivalents of the monoepoxide and 0.5 to 3 epoxide equivalents of the diepoxide per mole of a tetravalent metal halide, and 1.7 to 2.5 epoxide equivalents of monoepoxide and 0.25 to 2 epoxide equivalents per mole of the trivalent metal halide.

In accordance with one embodiment of the invention, use can be made of 2 or more epoxide equivalents of a diepoxide with a tetravalent metal halide, and the reaction product contains compounds which contain a free epoxide group. Such compounds are represented by the formulae:

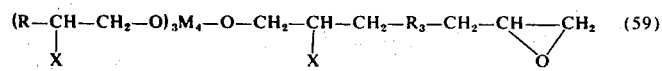  (59)

and

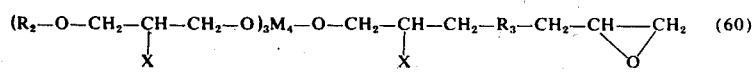  (60)

where R, $R_2$, $R_5$ and X are as defined above, and $M_4$ is one of the foregoing tetravalent metals.

Representative of the compounds which can be separated from reaction mixtures of the type described include the following:

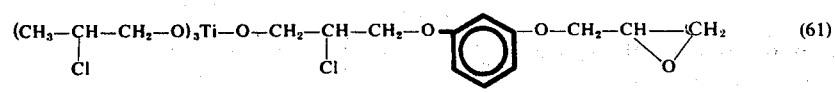  (61)

(TiCl$_4$ 1 mole; propylene oxide 3 epoxide equivalents; ERE 1359 2 epoxide equivalents)

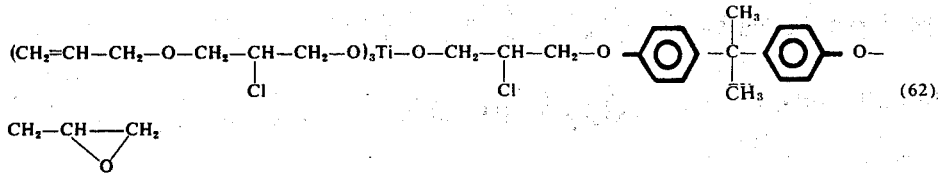  (62)

(TiCl$_4$ 1 mole; allyl glycidyl ether 3 epoxide equivalents; DER 332 2 epoxide equivalents)

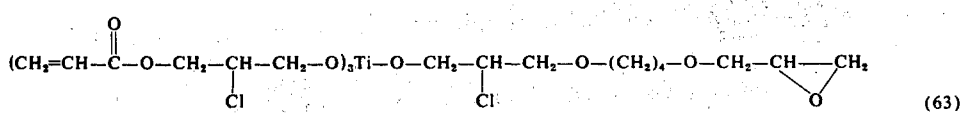  (63)

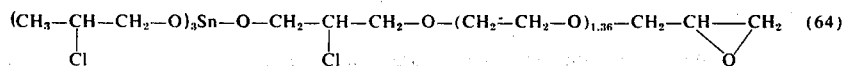  (64)

(TiCl$_4$ 1 mole; glycidyl acrylate 3 epoxide equivalents; RD 2 epoxide equivalents)

(SnCl$_4$ 1 mole; propylene oxide 3 epoxide equivalents; DER 736 2 epoxide equivalents)

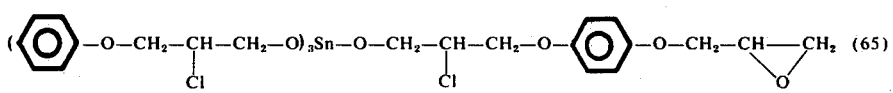  (65)

(SnCl$_4$ 1 mole; phenyl glycidyl ether 3 epoxide equivalents; ERE 1359 2 epoxide equivalents)

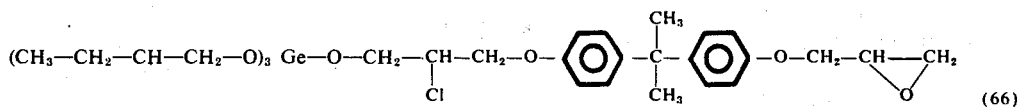  (66)

(GeCl$_4$ 1 mole; butylene oxide 3 epoxide equivalents; DER 332 2 epoxide equivalents)

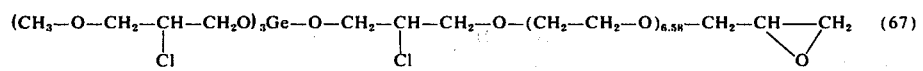  (67)

(GeCl$_4$ 1 mole; methyl glycidyl ether 3 epoxide equivalents; DER 508 2 epoxide equivalents)

Analogous compounds can be formed from antimony halides, except that use is made of one less epoxide equivalent of the monoepoxide. Representative compounds include the following:

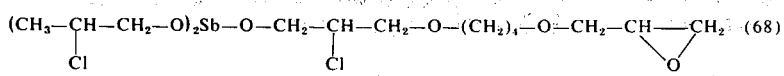  (68)

(SbCl₃ 1 mole; propylene oxide 2 epoxide equivalents; RD 2 2 epoxide equivalents)

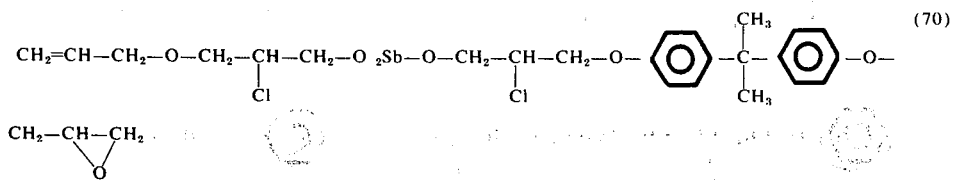 (69)

(SBCl₃ 1 mole; glycidyl acrylate 2 epoxide equivalents; ERE 1359 2 epoxide equivalents)

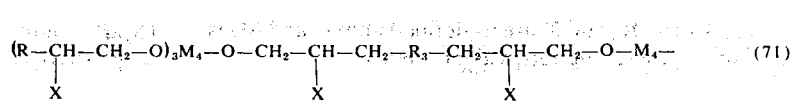

(SbCl₃ 1 mole; allyl glycidyl ether 2 epoxide equivalents; DER 332 2 epoxide equivalents)

In accordance with another embodiment of the invention, it has been found that the nature of the product can be changed by employing an amount of the diepoxide within the range of 0.5 to 1.8 epoxide equivalents per mole of the metal halides. As in the case of the previous embodiment, the product of the reaction is a mixture, but the product can be subjected to separation techniques to isolate the major components of the reaction product.

One of the major components of such reaction products include the following compounds:

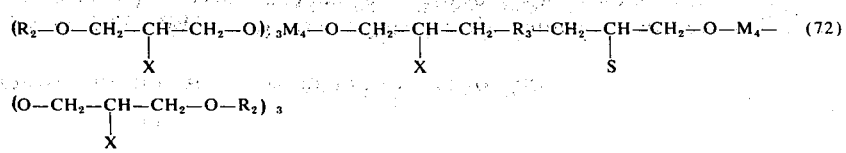 (70)

$$(R-\underset{X}{CH}-CH_2-O)_3M_4-O-CH_2-\underset{X}{CH}-CH_2-R_3-\underset{X}{CH_2-CH}-CH_2-O-M_4- \quad (71)$$

$$(O-CH_2-\underset{X}{CH}-R)_3$$

or $$(R_2-O-CH_2-\underset{X}{CH}-CH_2-O)_3M_4-O-CH_2-\underset{X}{CH}-CH_2-R_3-CH_2-\underset{S}{CH}-CH_2-O-M_4- \quad (72)$$

$$(O-CH_2-\underset{X}{CH}-CH_2-O-R_2)_3$$

Representative of such compounds include the following:

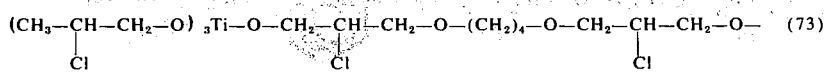 (73)

(TiCl₄ 1 mole; propylene oxide 3 epoxide equivalents; RD2 1 epoxide equivalent)

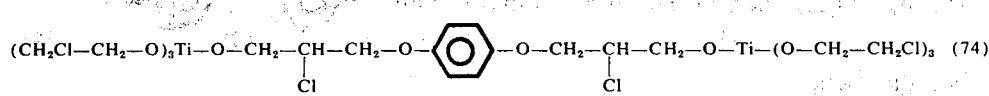 (74)

(TiCl₄ 1 mole; ethylene oxide 3 epoxide equivalents; ERE 1359 1 epoxide equivalent)

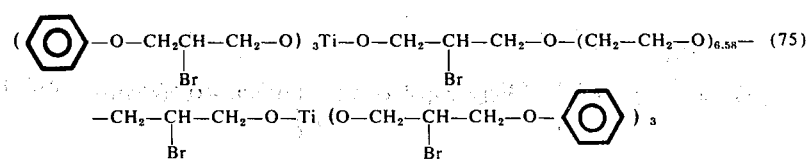 (75)

(TiBr₄ 1 mole; phenyl glycidyl ether 3 epoxide equivalents; DER 508 1 epoxide equivalent)

(SnCl₄ 1 mole; methyl glycidyl ether 3 epoxide equivalents, RD2 1 epoxide equivalent)

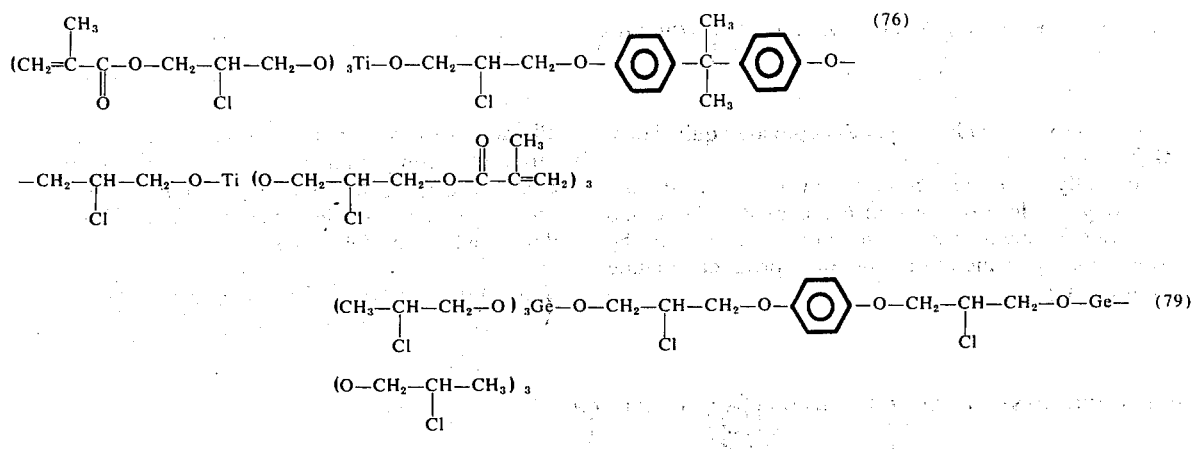

(TiCl₄ 1 mole; glycidyl methacrylate 3 epoxide equivalents; DER 332 1 epoxide equivalent)

(GeCl₄ 1 mole; propylene oxide 3 epoxide equivalents; ERE 1359 1 epoxide equivalent)

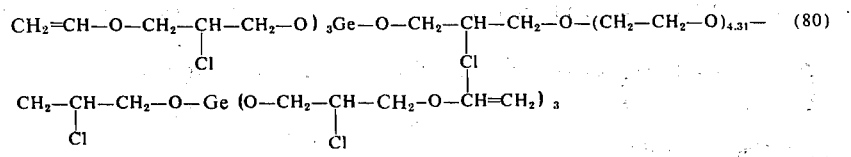

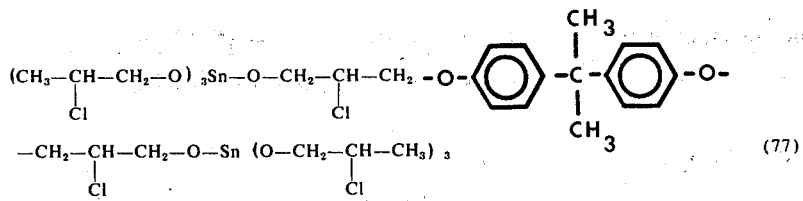

(GeCl₄ 1 mole; vinyl glycidyl ether 3 epoxide equivalents; DER 732 1 epoxide equivalent)

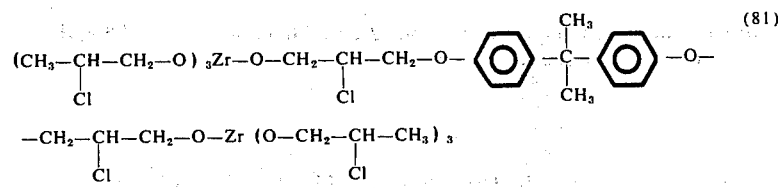

(SnCl₄ 1 mole; propylene oxide 3 epoxide equivalents; DER 332 1 epoxide equivalent)

(ZrCl₄ 1 mole; propylene oxide 3 epoxide equivalents; DER 332 1 epoxide equivalent)

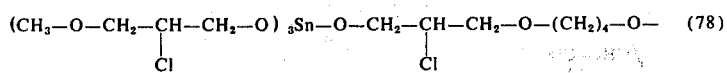

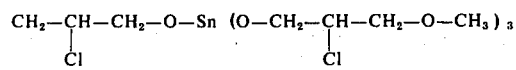

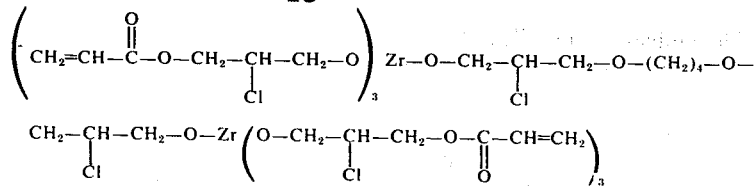
(82)

(ZrCl$_4$ 1 mole; glycidyl acrylate 3 epoxide equivalents; RD2 1 epoxide equivalent)

Generally analogous products can be produced from antimony halides, except that use is made of one less epoxide equivalent of the monoepoxide because of the lower valency of the antimony. Such products include the following:

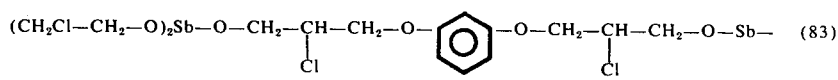  (83)

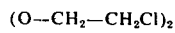

(SbCl$_3$ 1 mole; ethylene oxide 2 epoxide equivalents; ERE 1359 1 epoxide equivalent)

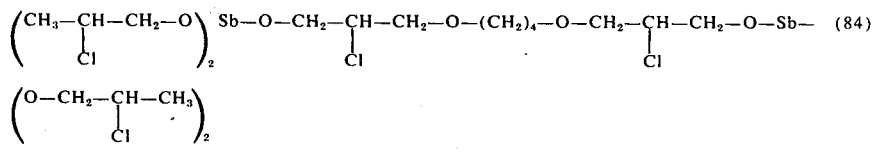 (84)

(SbCl$_3$ 1 mole; propylene oxide 2 epoxide equivalents; RD2 1 epoxide equivalent)

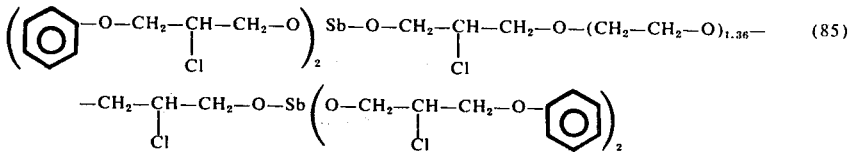 (85)

(SbCl$_3$ 1 mole; phenyl glycidyl ether 2 epoxide equivalents; DER 736 1 epoxide equivalent)

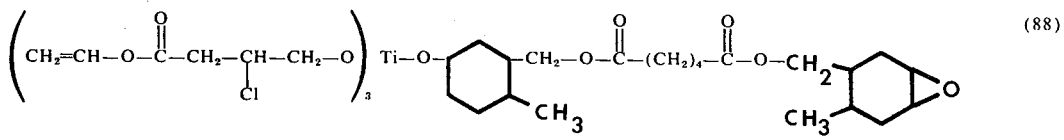 (88)

Reactions of the type described above with respect to the diepoxides can also be carried out using the cycloalkane epoxides. Reactions of this type also include a mixture of compounds including complex compounds containing a beta-haloalkoxy group. Representative of the compounds included in such reaction products are illustrated by the following:

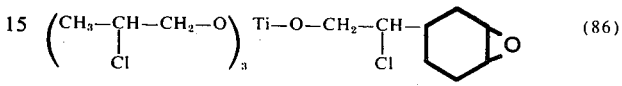 (86)

(TiCl$_4$ 1 mole; propylene oxide 3 epoxide equivalents; RD4 2 epoxide equivalents)

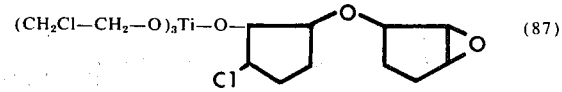 (87)

(TiCl$_4$ 1 mole; ethylene oxide 3 epoxide equivalents; ERR 4205 2 epoxide equivalents)

(TiCl$_4$ 1 mole; glycidyl acrylate 3 epoxide equivalents; ERR 4289 2 epoxide equivalents)

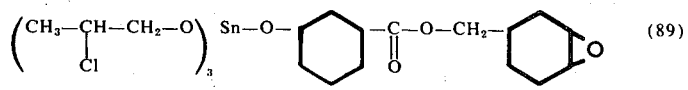 (89)

(SnCl₄ 1 mole; propylene oxide 3 epoxide equivalents; ERR 4221 2 epoxide equivalents)

(GeCl₄ 1 mole; ethylene oxide 3 epoxide equivalents; RD4 2 epoxide equivalents)

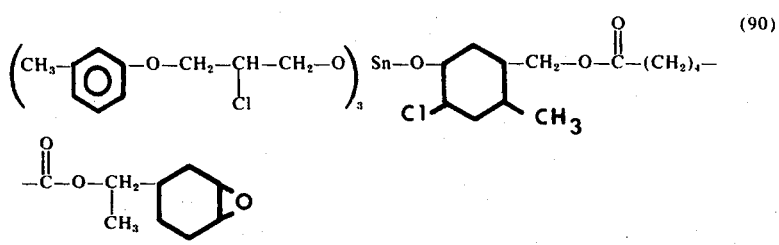
(90)

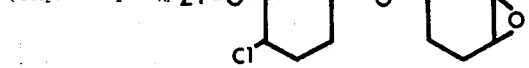
(92)

(SnCl₄ 1 mole; cresyl glycidyl ether 3 epoxide equivalents; ERR 4289 2 epoxide equivalents)

(ZrCl₄ 1 mole; ethylene oxide 3 epoxide equivalents; ERR 4205 2 epoxide equivalents)

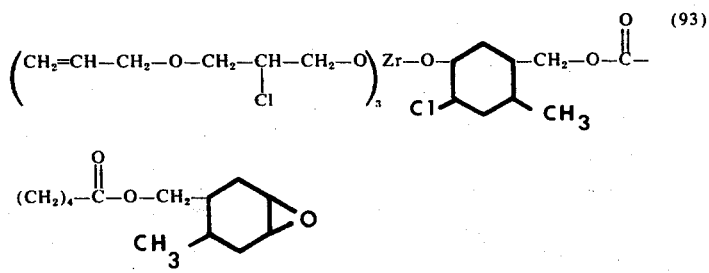
(93)

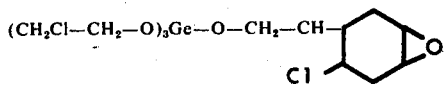
(91)

(ZrCl₄ 1 mole; allyl glycidyl ether 3 epoxide equivalents; ERR 4289 2 epoxide equivalents)

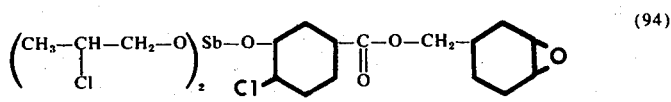
(94)

(SbCl₃ 1 mole; propylene oxide 2 epoxide equivalents; ERR 4221 2 epoxide equivalents)

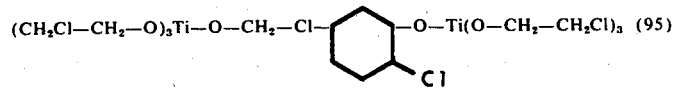
(95)

(TiCl₄ 1 mole; ethylene oxide 3 epoxide equivalents; RD4 1 epoxide equivalent)

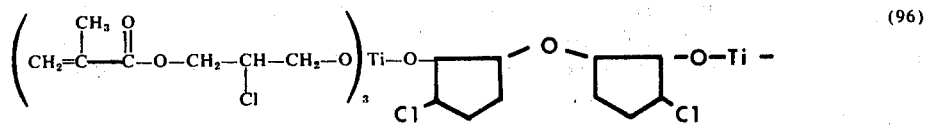
(96)

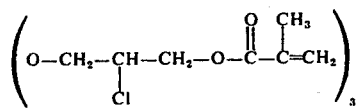

(TiCl₄ 1 mole; glycidyl methacrylate 3 epoxide equivalents; ERR 4205 1 epoxide equivalent)

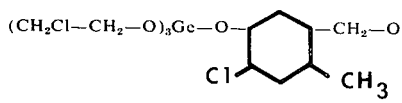 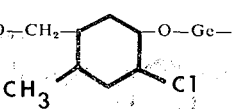 (97)

(GeCl₄ 1 mole; ethylene oxide 3 epoxide equivalents; ERR 4289 1 epoxide equivalent)

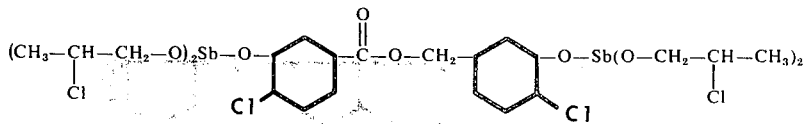 (98)

(SbCl₃ 1 mole; propylene oxide 2 epoxide equivalents; ERR 4221 1 epoxide equivalent)

The compounds of the present invention, or mixtures of the compounds of the present invention, are particularly well suited for use in the treatment of glass to include glass fibers to impart to the glass a protective coating which renders the glass less susceptible to fatigue by abrasion. Because the chemical bonds between the metal and organic groups are more resistant to hydrolysis, the products of the present invention can be applied to glass surfaces without hydrolysis in the metal-organic group bond. For this purpose, the products of the present invention can be dissolved in an inert organic solvent such as diacetone, alcohol, acetone, etc., and applied to the glass surface. While it is not necessary to the practice of the present invention, the resulting coating can be heated to a temperature sufficient to result in decomposition of the products of this invention to thereby leave on the glass surface a metal oxide coating which is similarly capable of imparting abrasion resistance to the glass. In general, temperatures of 350°F. or higher may be used for this purpose when it is desired to form a metal oxide coating on the glass surface. However, in some instances a lower temperature may be employed.

The products of the present invention are also capable of being used as coupling agents to provide a more secure bonding relationship between glass fibers and thermosetting resinous material or elastomeric material. In this application, the products of this invention can be simply applied to the glass fiber surface, dried at a temperature below the decomposition temperature of the coating and then simply admixed with plastic materials or elastomeric materials whereby the products of this invention operate to establish a chemical bond between the glass fiber surfaces and resin or elastomeric material.

Having described the basic concepts of the present invention, reference is now made to the following examples which are provided by way of illustration, and not of limitation, in the practice of this invention in the preparation of the products of this invention.

EXAMPLE 1

Into a 2 liter round bottom flask equipped with a stirrer, a reflux condenser, an addition funnel and a thermometer, is placed 82.45 cc (0.75 moles) of titanium tetrachloride. To the TiCl₄ is added 500 cc of pentane, and then 262.1 cc of propylene oxide (3.75 moles) is added with a further addition of 1000 cc of pentane.

The reaction mixture is allowed to stand over night after which the pentane and excess propylene oxide is removed. The product is found to be tetrakis (beta-chloropropyl) titanate.

EXAMPLE 2

Using the procedure described in Example 1, 4.1 moles of ethylene oxide are reacted with 1 mole of titanium tetrachloride to produce the compound (23) described above.

EXAMPLE 3

Using the procedure described in Example 1, 4.0 moles of propylene oxide are reacted with 1 mole of stannic chloride. The product is found to be the beta-chloroalkoxy compound (26) described above.

EXAMPLE 4

The procedure of Example 1 is again repeated, using instead of TiCl₄, germanium tetrachloride. The product formed is found to be the beta-chloropropoxy compound (28).

EXAMPLE 5

The procedure of Example 1 is repeated, using 1 mole of antimony trichloride and 3.05 moles of propylene oxide. The product is the tris-beta-chloropropoxy compound (29).

EXAMPLE 6

One mole of titanium tetrachloride is reacted with 4 mole of phenyl glycidyl ether, using the procedure outlined in Example 1. The product of the reaction is found to be the titanate (31).

EXAMPLE 7

Using the procedure outlined in Example 1, one mole of titanium tetrachloride is reacted with 4.0 mole of allyl glycidyl ether. The product is found to be the beta-chloroallyl compound (33).

EXAMPLE 8

Using the procedure of Example 6, 1 mole of stannic chloride is reacted with 4.0 moles of methyl glycidyl ether. After removal of the solvent, the product is found to be the compound (37).

EXAMPLE 9

The procedure of Example 8 was repeated, except that the metal halide was germanium tetrachloride and the epoxide was cresyl glycidyl ether. The product was found to be the ester (40) described above.

EXAMPLE 10

The procedure of Example 6 was again repeated, using as the metal halide zirconium bromide and glycidyl acrylate in a mole ratio of 4.0 moles of the epoxide per mole of halide. The product was found to be compound (43) described above.

EXAMPLE 11

Using the procedure of Example 6, 3 moles of phenyl glycidyl ether were reacted with antimony trichloride. After removal of the solvent, the product was found to contain compound (45) described above.

EXAMPLE 12

Using the apparatus employed in Example 1, one mole of titanium tetrachloride is reacted with three moles (3 epoxide equivalents) of propylene oxide. The product of this reaction is then reacted with one mole of phenyl glycidyl ether. The reaction product is found to contain a mixture of compounds, and from this mixture there is separated the compound (48) described above.

EXAMPLE 13

Using the procedure described in Example 12, one mole of titanium tetrachloride is reacted with 2 moles of propylene oxide and the product of this reaction is then reacted with 2 moles of allyl glycidyl ether. The product of the reaction is a mixture of compounds which can be utilized as such. However, compound (50) described above can be separated therefrom using conventional separation techniques.

EXAMPLE 14

Using the procedure described in Example 12, one mole of stannic chloride is reacted with 3 moles of ethylene oxide and the product is then reacted with 1 mole of n-octyl glycidyl ether. The product of the reaction is a mixture of compounds from which there can be separated the compound (51) described above.

EXAMPLE 15

Using the procedure described in Example 12, 1 mole of germanium tetrachloride is reacted with 3 moles of ethylene oxide and 1 mole of vinyl glycidyl ether. Such a product is a mixture from which there can be separated the compound (57).

EXAMPLE 16

The procedure of Example 12 is repeated, using 1 mole of zirconium tetrachloride, 3 moles of propylene oxide and 1 mole of glycidyl methacrylate. The reaction product is a mixture of compounds which is found to contain compound (55). If desired, this compound can be separated from the reaction mixture.

EXAMPLE 17

The procedure of Example 12 is again repeated, using antimony trichloride (1 mole), 1 mole of propylene oxide and 2 moles of vinyl glycidyl ether. The product is found to contain a mixture of compounds from which can be separated, if desired, compound (57) described above.

EXAMPLE 18

Using the procedure described in Example 12, one mole of titanium tetrachloride is reacted with 3 moles of propylene oxide and 1 mole (2 epoxide equivalents) of ERE 1359. Addition of the propylene oxide is made prior to the addition of the diepoxide, and the product is found to contain a mixture of compounds, including compound (61) which can be separated from the reaction mixture, if desired, by conventional techniques.

EXAMPLE 19

Using the procedure of Example 18, one mole of titanium tetrachloride is reacted with 3 moles of allyl glycidyl ether and 1 mole (2 epoxide equivalents) of DER 332. The reaction product is a mixture from which compound (62) can be separated.

EXAMPLE 20

Using the procedure of Example 18, one mole of stannic chloride is reacted with 3 moles of propylene oxide. The product of this reaction is then reacted with 1 mole of DER 736, and the product of this reaction is a mixture including compound (64).

EXAMPLE 21

Using the procedure of Example 20, 1 mole of zirconium tetrachloride is reacted with 3 moles of propylene oxide, and the product of this reaction is reated with 1 mole of DER 332. The product is a mixture of compounds.

EXAMPLE 22

One mole of antimony trichloride is reacted with 2 moles of ethylene oxide and the product of this reaction is then reacted with 1 mole of RD 2. The product is a mixture which is found to include compound (68) which can be separated therefrom by conventional techniques.

EXAMPLE 23

Using the procedure of Example 12, one mole of titanium tetrachloride is reacted with 3 moles of propylene oxide in the presence of pentane as a solvent. The product of this reaction is then reacted with 0.5 mole (1 epoxide equivalent) of RD 2. The product of the reaction is a complex mixture of titanium ortho-esters. The mixture is found to contain compound (73) which can be separated therefrom, if desired, by conventional techniques.

EXAMPLE 24

The procedure of Example 23 is repeated, using 1 mole of titanium tetrabromide, 3 moles of phenyl glycidyl ether and 0.5 moles of DER 508. The product of the reaction is found to be a complex mixture of titanium ortho-esters including compound (75) described above.

EXAMPLE 25

Using the procedure of Example 23, one mole of stannic chloride is reacted with 3 moles of propylene oxide and the product of this reaction is reacted with 0.5 moles of DER 332. The product of the reaction is a complex mixture which is found to include compound (77). The latter is separated from the reaction product by means of extraction.

EXAMPLE 26

The procedure of Example 23 is again repeated, using germanium tetrachloride, propylene oxide and ERE 1359. The product is found to contain the ester (79) which can be separated from the mixture by conventional techniques.

EXAMPLE 27

The procedure of Example 23 is repeated, using 1 mole of zirconium tetrachloride, 3 moles of propylene oxide and 0.5 moles of DER 332. The product of the reaction is found to include compound (81) which can be separated therefrom, if desired.

EXAMPLE 28

Using the procedure of Example 23, one mole of antimony trichloride is reacted with 2 moles of ethylene oxide and 0.5 moles of ERE 1359. The product of the reaction which is a complex mixture contains compound (83) which can be separated therefrom.

EXAMPLE 29

Using the procedure of Example 23, one mole of titanium tetrachloride is reacted with 3 moles of propylene oxide. The product of this reaction is then reacted with 1 mole of the cyclohexane epoxide RD 4. The product is a complex mixture of compounds and it was found that the mixture includes compound (86) which can be separated therefrom, if desired.

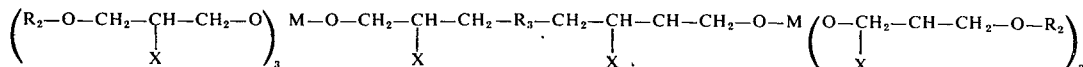

EXAMPLE 30

Using the procedure of Example 23, one mole of titanium tetrachloride is reacted with 3 moles of glycidyl methacrylate and the product of this reaction is then reacted with 1 epoxide equivalent (0.5 mole) of the diepoxide ERR 4205. The product of the reaction is a mixture of compounds which is found to include compound (96).

It will be apparent from the foregoing that numerous changes and modifications can be made in the details of procedure, formulation and use without departing from the spirit of the invention, especially as defined in the following claims.

We claim:

1. A compound having the formula

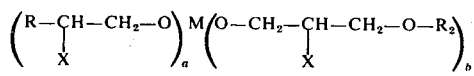

wherein M is a tetravalent metal selected from the group consisting of titanium, tin, germanium and zirconium, R is hydrogen or alkyl, $R_2$ is a group of the formula

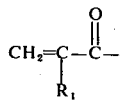

wherein $R_1$ is hydrogen or methyl, X is halogen, $a$ and $b$ are each integers from 1 to 3, with the sum of $a$ and $b$ being equal to 4.

2. A compound as defined in claim 1 wherein X is chlorine or bromine.

3. A compound as defined in claim 1 wherein M is titanium.

4. A compound as defined in claim 1 wherein $a$ is 3 and $b$ is 1.

5. A compound having the formula

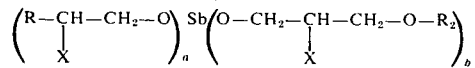

wherein R is hydrogen or alkyl, X is halogen, $R_2$ is a group of the formula

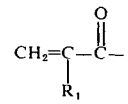

wherein $R_1$ is hydrogen or methyl, and $a$ and $b$ are each integers from 1 to 2, with the sum of $a$ and $b$ being equal to 3.

6. A compound as defined in claim 5 wherein X is chlorine or bromine.

7. A compound as defined in claim 5 wherein $a$ is 2 and $b$ is 1.

8. A compound of the formula

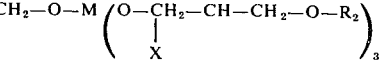

wherein M is a tetravalent metal selected from the group consisting of titanium tin, germanium and zirconium, X is halogen, R is hydrogen or alkyl, $R_2$ is selected from the group consisting of aryl, alkyl, alkenyl and a group of the formula

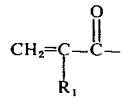

wherein $R_1$ is hydrogen or methyl and $R_3$ is a divalent organic group selected from the group consisting of alkylene, alkyleneoxyalkylene, oxyalkyleneoxy, oxyalkyleneoxyalkyleneoxy, a group having the formula

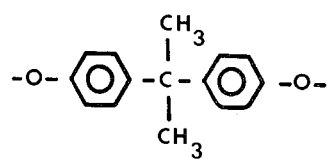

and a group having the formula

9. A compound as defined in claim 8 wherein X is chlorine or bromine.

10. A compound as defined in claim 8 wherein M is titanium.

11. A compound selected from the group consisting of
1. a compound of the formula

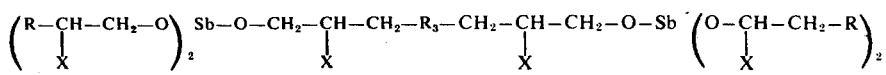

and
2. a compound of the formula

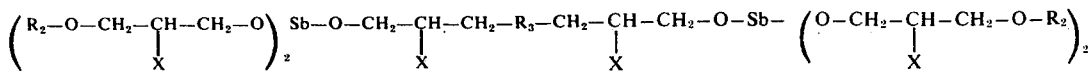

wherein X is halogen, R is hydrogen or alkyl, $R_2$ is selected from the group consisting of aryl, alkyl, alkenyl and a group of the formula

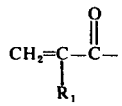

wherein $R_1$ is hydrogen or methyl, and $R_3$ is a divalent organic group selected from the group consisting of alkylene, alkyleneoxyalkylene, oxyalkyleneoxy, oxyalkyleneoxyalkyleneoxy, a group having the formula

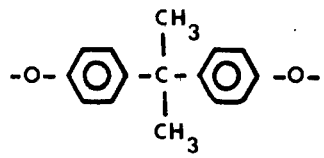

and a group having the formula

12. A compound as defined in claim 11 wherein X is chlorine or bromine.

13. A method of preparing organo metallic compounds by contacting, in the liquid stage, (1) an antimony halide and (2) an alkylene oxide having the formula

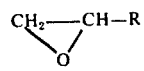

wherein R is hydrogen or alkyl, and (3) an epoxide having the formula

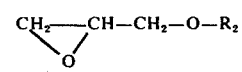

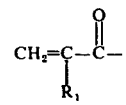

wherein $R_2$ is a group of the formula

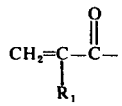

wherein $R_1$ is hydrogen or methyl.

14. The method of claim 13 in which from 1 to 2 epoxide equivalents of (2) are contacted with 1 to 2 epoxide equivalents of (3) per mole of antimony halide.

15. the method of claim 13 in which the antimony halide is antimony chloride or antimony bromide.

16. The method of claim 13 in which the reaction produced includes compounds having the formula

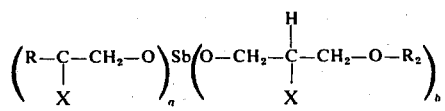

wherein X is halogen and $a$ and $b$, each, are integers from 1 to 2 with the sum of $a$ and $b$ being equal to 3.

* * * * *